United States Patent [19]

Sprinkle

[11] 4,219,538

[45] Aug. 26, 1980

[54] RADIOIODINATION PROCESS

[75] Inventor: Leslie M. Sprinkle, St. Louis, Mo.

[73] Assignee: Mallinckrodt, Inc., St. Louis, Mo.

[21] Appl. No.: 875,256

[22] Filed: Feb. 6, 1978

[51] Int. Cl.$^2$ ............................................. A61K 43/00
[52] U.S. Cl. ...................................................... 424/1
[58] Field of Search ........................... 424/1; 23/230 B

[56] References Cited

U.S. PATENT DOCUMENTS 4,088,746   5/1978   Blakemore et al. ...................... 424/1

OTHER PUBLICATIONS

Stagg, B. H., et al., Nature 228, 58-59(1970).
Goldfing et al., Endocrinology, vol. 95, No. 5, Nov., 1974, pp. 1228-1233.

Primary Examiner—Brooks H. Hunt
Assistant Examiner—Christine M. Nucker
Attorney, Agent, or Firm—Roy J. Klostermann

[57] ABSTRACT

An improved process for radioiodinating thyroid stimulating hormone.

5 Claims, No Drawings

RADIOIODINATION PROCESS

This invention relates to a process for radioiodinating human thyroid stimulating hormone (hereinafter sometimes referred to as TSH) and to such radioiodinated TSH.

The most frequently used method for radioiodinating TSH is the chloramine-T method described by Hunter and Greenwood, *Nature* 194, 495 (1962). It involves radioiodinating TSH utilizing chloramine-T as an oxidizing agent. Chloramine-T aids in introducing the iodine into the TSH molecule. This method provides radioiodinated TSH having sufficient radioactivity needed for its use in radioimmunoassays. However, this radiolabelling procedure often causes partial degradation of the TSH during iodination which is called iodination damage. Iodination damage results in iodinated TSH having only partial immunoreactivity. Further, there is a tendency for radioiodinated TSH on aging to spontaneously disassociate into various products as a consequence of radioactive decay which is often referred to as the decay (catastrophe) phenomenon. This decay catastrophe results in further loss of immunoreactivity. Such loss of immunoreactivity of course is disadvantageous in the radioimmunoassay for thyrotropin.

Although immunoreactivity of TSH may be increased with short iodination reaction times, radioactivity is decreased resulting in unsatisfactory counting times in subsequent radioimmunoassays. Further, reducing the amount of chloramine-T does not markedly increase immunoreactivity. Therefore, the prior art process balances reduced iodination damages against ultimate count rates.

An object of this invention is to provide for radioiodinating TSH utilizing chloramine-T to a suitable radioactivity for use in subsequent radioimmunoassays, with an increased immunoreactivity and a reduced loss of such immunoreactivity over extended storage periods.

In accordance with this invention there is provided an improvement in the process where TSH is radioiodinated under radioiodinating conditions to a suitable radioactivity e.g., 40 to 100 microcuries per microgram of TSH utilizing a suitable oxidant, e.g., chloramine-T and where the immunoreactivity of said TSH degrades during the radioiodination reaction or aging thereafter which involves including during the radioiodination reaction to reduce said degradation a protecting amount of a sulfoxide protective agent including those having the following formula:

$$\underset{RSR}{\overset{\overset{\displaystyle O}{\|}}{}}$$

wherein each R is a substituted or unsubstituted alkyl, e.g. containing 1 to 10 carbon atoms including lower alkyl containing 1 to 4 carbon atoms such as methyl, ethyl, propyl and butyl, phenyl, benzyl or tolyl.

Examples of such protective agents include dimethyl sulfoxide (DMSO), diethyl sulfoxide, methyl, ethyl sulfoxide, dipentyl sulfoxide, dioctyl sulfoxide, diphenyl sulfoxide, dibenzyl sulfoxide and ditolyl sulfoxide. It is advantageous to use DMSO.

A general description of the aforementioned radioiodination process may be found in Hunter and Greenwood.

The radioiodination is carried out under radioiodinating conditions utilizing a sufficient amount of a suitable radioiodinating agent, e.g., Na$^{125}$I, to give the desired activity. Such conditions include suitable reaction times, e.g., 15 seconds to 4 minutes and reaction temperatures, e.g. 4° C. to 25° C. and the use of a buffer, e.g., sodium phosphate 0.5 M, to maintain the pH at 4–9 during the reaction. Chloramine-T is generally used in oxidizing amounts, e.g., from about 0.25 microgram to about 15 micrograms preferably from about 0.5 to about 10 micrograms per microgram of TSH.

In accordance with the present invention the protective agent is present during the radioiodination reaction, preferably during the whole reaction. Advantageously, the protective agent is added before the radioiodinating agent. It is used in protecting amounts, e.g. from about 0.9 to about 11 milligrams per microgram of TSH.

A suitable reducing agent, e.g. sodium metabisulfite is used to quench the reaction in a quenching amount. For example, sodium metabisulfite is used in an amount of from about 25 to about 125, preferably from about 1 to about 50 micrograms per microgram of TSH.

The radioiodinated TSH is recovered by the usual methods, e.g., column chromatography.

The following examples illustrate the invention. All parts are by weight unless otherwise stated.

EXAMPLES 1–7

Materials and Methods

Reagents
(1) Human thyroid stimulating hormone suitable for labelling.
(2) Primary antibody; anti-human thyroid stimulating hormone.
(3) Standard human thyroid stimulating hormone; standardized to the MRC 68/38 standard from the Medical Research Council, Mill Hill, London, England.
(4) Trishydroxymethylaminomethane.
(5) Bovine gamma globulin.
(6) Sodium phosphate, monobasic and dibasic.
(7) Na$^{125}$I.
(8) Human Serum Albumin.
(9) Precipitating Antibody; in Rabbits using Guinea Pig Immunoglobulin-G.
(10) Chloramine-T.
(11) Sodium Metabisulfite.
(12) Dimethyl Sulfoxide.

Iodination Procedure

The quantities of the reagents used in Examples 1–17 are listed in Table 1 along with the results.

A small quantity of 0.5 M sodium phosphate buffer was added to TSH suitable for labelling to reduce pH fluctuations during the reaction. To this was added, if used, DMSO and then Na$^{125}$I. Chloramine-T dissolved in 0.05 M sodium phosphate buffer was added next. Sodium metabisulfite was utilized to stop the oxidation reaction.

Immediately subsequent to the addition of sodium metabisulfite, the entire reaction mixture was applied to a chromatography column containing pre-swelled Sephadex G-75-40 or G-75-120 for separation of $^{125}$I-TSH from unreacted (free) $^{125}$I. Ten drop fractions were collected and evaluated on an individual basis by radioimmunoassay prior to pooling.

Assay Procedure

Therefore, total antibody binding equals 50% in this example.

TABLE 1

| NO. | TSH | 0.5M Sodium Phosphate Buffer | Na$^{125}$I | DMSO | Chloramine-T | Reaction Time at Room Temperature | Sodium Metabisulfite | Chromatography | Max % Binding |
|---|---|---|---|---|---|---|---|---|---|
| 1 | 2.5μg | 10μl | 0.25 mCi | NONE | 25μg | 4 min. | 125μg | Sephadex G-75-40 | 44.2% |
| 2 | " | " | 0.5 mCi | " | " | 30 sec. | " | Sephadex G-75-40 | 44.8% |
| 3 | " | " | " | " | " | 10 sec. | " | Sephadex G-75-40 | 40.8% |
| 4 | " | " | " | " | " | 15 sec. | " | Sephadex G-75-40 | 38.0% |
| 5 | " | " | " | 5μl | " | " | " | Sephadex G-75-40 | 44.6% |
| 6 | 2.5μg | 10μl* | " | " | " | " | " | Sephadex G-75-120 | 28.6%** |
| 7 | 2.5μg | 10μl | " | NONE | " | " | " | Sephadex G-75-120 | 26.9% |
| 8 | " | " | 1.0 mCi | " | " | " | " | Sephadex G-75-120 | 26.9% |
| 9 | " | " | 0.5 mCi | " | " | 30 sec. | " | Sephadex G-75-120 | 31.3% |
| 10 | " | 10μl*** | " | " | " | 4 min @ 4° C. | " | Sephadex G-75-120 | 31.0% |
| 11 | 10μg | 25μl | 2.5 mCi | " | 10μg | 15 sec. | 25μg | Sephadex G-75-120 | 38.8% |
| 12 | " | " | " | " | " | " | " | Sephadex G-75-120 | 49.5% |
| 13 | 25μg | " | " | " | " | " | " | Sephadex G-75-120 | 47.8% |
| 14 | " | " | " | " | " | " | " | Sephadex G-75-120 | 51.5% |
| 15 | 20μg | " | " | 5μl | " | " | " | Sephadex G-75-120 | 50.4% |
| 16 | " | " | " | " | " | " | " | Sephadex G-75-120 | 52.6% |
| 17 | " | " | " | " | " | " | " | Sephadex G-75-120 | 43.7% |

*10-fold reduction in buffer molarity to 0.05M
**Different 2% antibody utilized in assay; different technician
***0.5M KPO$_4$ buffer In order to determine immunoreactivity or total antibody binding of the radiolabelled TSH, the material is tested in a radioimmunoassay method. According to this method a fixed amount of primary antisera (anti-human TSH) is added in a tube to a serum substitute equivalent to TSH-free human serum. Radioiodinated TSH is also added in a buffer solution, diluted to a count rate appropriate for radioimmunoassay. This mixture of antibody, serum substitute and radiolabelled antigen is incubated for a predetermined period prior to the addition of a secondary (precipitating) antisera. The precipitating antisera functions as a method to separate antibody-bound from free 125 I-TSH. The final separation is completed by centrifugation, during which the primary-secondary antibody complex goes to the bottom of the tube, as does any antibody-bound 125 I-TSH. The unbound 125 I-TSH is simply removed by decantation. The percent antibody binding is determined by dividing the number of radioactive counts in each tube after decantation by the number of counts initially added to each tube at the beginning of the assay.

| Example: | Counts/min. at beginning of assay | 20,000 |
|---|---|---|
| | Counts/min. at end of assay after decantation | 10,000 |
| | 10,000 cpm/20,000 cpm = | 50% |

EXAMPLE 18

Following the procedure listed for Examples 1–17 and using 5 microliters of DMSO, two lots of 125 I labelled TSH were prepared having a specific radioactivity of 58.6 microcuries per microgram for lot 1 and 80.9 microcuries per microgram for lot 2. Stability studies at room temperature were carried out with the following results.

| LOT 1 | |
|---|---|
| Test Time | Total % Binding |
| Initial | 39.04% |
| 3 weeks | 30.38% |
| 4 weeks | 26.40% |
| 5 weeks | 27.24% |
| 6 weeks | 25.12% |
| 7 weeks | 23.33% |

The average loss in % binding over seven weeks was 2.24% per week.

| Lot 2 | |
|---|---|
| Test Time | Total % Binding |
| Initial | 41.4% |
| 1 week | 35.16% |
| 2 weeks | 33.98% |
| 3 weeks | 32.57% |

-continued

Lot 2

| Test Time | Total % Binding |
|---|---|
| 5 weeks | 28.77% |
| 6 weeks | 28.55% |
| 7 weeks | 26.58% |
| 8 weeks | 25.09% |
| 9 weeks | 25.40% |

The average loss in % binding over nine weeks was 1.75% per week.

What is claimed:

1. In a process for radioiodinating TSH under radioiodinating conditions to a radioactivity of 40 to 100 microcuries per micrograms suitable for use in RIA procedures utilizing chloramine-T wherein the immunoreactivity of said TSH degrades during the radioiodination reaction or aging thereafter, the improvement comprising additionally including during the radioiodination reaction to reduce said degradation a protecting amount of a protective agent represented by the formula $$\underset{RSR}{\overset{O}{\parallel}}$$

wherein each R is lower alkyl, phenyl, benzyl or tolyl.

2. A process according to claim 1 wherein the protective agent is present in an amount of from about 0.1 to about 11 milligrams per microgram of TSH.

3. A process according to claim 2, wherein said protective agent is dimethyl sulfoxide.

4. A radioiodinated TSH prepared by the process of claim 1.

5. A radioiodinated TSH prepared by the process of claim 2.